United States Patent [19]

Lafon

[11] 3,944,549
[45] Mar. 16, 1976

[54] AMINO DERIVATIVES OF 1,4-BENZODIOXAN

[75] Inventor: Louis Lafon, Paris, France

[73] Assignee: Laboratoire L. Lafon, Alfort, France

[22] Filed: Oct. 23, 1973

[21] Appl. No.: 408,947

[30] Foreign Application Priority Data
Oct. 24, 1972 United Kingdom............... 49022/72

[52] U.S. Cl. 260/256.4 N; 260/268 BC; 260/340.3; 424/250; 424/251
[51] Int. Cl.²........................................ C07D 239/24
[58] Field of Search................ 260/256.4 N, 268 BC

[56] References Cited
UNITED STATES PATENTS
3,312,592  4/1967  Chodnekar et al............ 260/268 BC
3,496,183  2/1970  Toldy et al. .................. 260/268 BC

*Primary Examiner*—Richard J. Gallagher
*Assistant Examiner*—James H. Turnipseed

[57] ABSTRACT

1-[2-(1,4-benzodioxanyl)methyl]-4-(2-hydroxyethyl)-piperazine hemifumarate and the related compounds of formula:

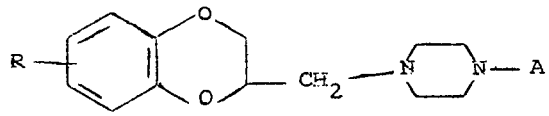

in which R is hydrogen or alkyl; and A is $-Z-OR_1$, $-CH_2CHOR''_1CH_2OR'_1$, $-Z-CO-B$ or amidino, where Z is a linear or branched divalent hydrocarbon chain of 1 to 3 carbon atoms, $R'_1$ and $R''_1$, which may be identical or different, are each hydrogen, alkyl, or acyl, B is OH, alkoxy, or a secondary, tertiary or N-heterocyclic amino radical, and $R_1$ is alkyl, acyl other than nicotinoyl or 3,4,5-trimethoxy-benzoyl, or, when R is other than hydrogen, hydrogen, and its acid addition salts, are useful in therapy as vasodilators and α-blocking agents.

8 Claims, No Drawings

AMINO DERIVATIVES OF 1,4-BENZODIOXAN

The present invention relates to amino derivatives of 1,4-benzodioxan, their preparation and their use.

TOLDY et al. (Acta Chimica Academiae Scientiarium Hungaricae (1966), 49, 265–286) investigated 1-[2-(1,4-benzodioxanyl)-methyl]-4-(2-hydroxyethyl)-piperazine as an agent for the treatment of digestive ulcers; they stated that it was devoid of such activity.

It has now been found, surprisingly, that the 1,4-benzodioxan derivatives of the formula given below are useful in the treatment of cardiovascular illnesses and are better tolerated than the known product mentioned above.

The new amino derivatives of 1,4-benzodioxan of the invention are a. 1-[2-(1,4-benzodioxanyl)-methyl]-4-(2-hydroxyethyl)-piperazine hemifumarate, and
b. the compounds of the formula:

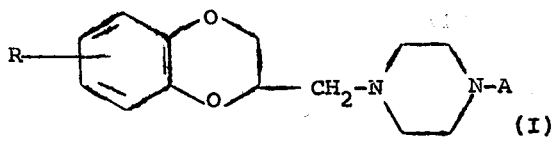

in which R is hydrogen or alkyl and A is $-Z-OR_1$, $-CH_2CHOR''_1CH_2OR'_1$, $-Z-CO-B$ or amidino, where Z is a linear or branched divalent hydrocarbon chain of 1 to 3 carbon atoms, $R'_1$ and $R''_1$, which may be identical or different, are each hydrogen, alkyl, or acyl, B is OH, alkoxy, or a secondary, tertiary of N-heterocyclic amino radical, and $R_1$ is alkyl, acyl other than nicotinoyl or 3,4,5-trimethoxybenzoyl, or when R is other than hydrogen, hydrogen, and their acid addition salts.

By amidino group is to be understood as a group possessng the structure $-C(NH_2):NH$ optionally substituted on one or both nitrogens, or a group of formula:

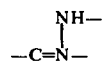

included in a ring. Examples of such cyclic amidino groups are 2-imidazolyl, 2-pyrimidinyl, 2-$\Delta^2$-imidazolidinyl and 2-(1,4,5,6-tetrahydropyrimidinyl).

Preferred compounds, in addition to 1-[2-(1,4-benzodioxanyl)-methyl]-4-(2-hydroxyethyl)-piperazine hemifumarate, include the compounds of the formula:

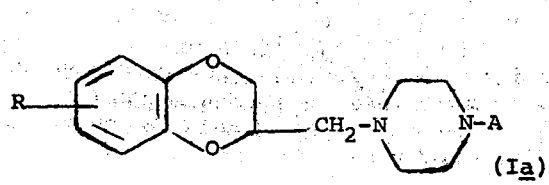

in which R is hydrogen or alkyl of 1 to 5 carbon atoms, and A is $-CH_2CH_2OR_1$, $-CH_2CHOR''_1CHOR'_1$, 2-pyrimidinyl or $-CH_2COB$ where $R'_1$ and $R''_1$, which may be identical or different, are each hydrogen, alkyl of 1 to 5 carbon atoms, alkanoyl of 1 to 5 carbon atoms, $R_1$ is alkyl of 1 to 5 carbon atoms, alkanoyl of 1 to 5 carbon atoms, or when R is other than hydrogen, hydrogen, and B is a secondary, tertiary or N-heterocyclic amino radical, e.g. 2,6-dimethylanilino-; and their acid addition salts.

The compounds of the invention may be made by reacting a 1,4-benzodioxan derivative of formula

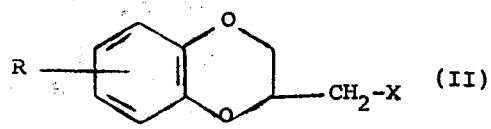

wherein X is halogen, preferably chlorine, or methanesulphonyloxy and R is as defined above, with a compound of the formula:

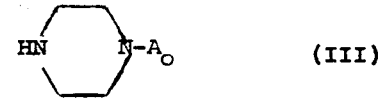

wherein $A_o$ is A as defined above, or, when R is hydrogen, $CH_2CH_2OH$, and optionally converting a base obtained into an acid addition salt thereof. The reaction may be carried out in a solvent at the reflux temperature of the latter.

According to a variant of this process, a compound of the formula II is reacted with piperazine and the product obtained, which has the formula:

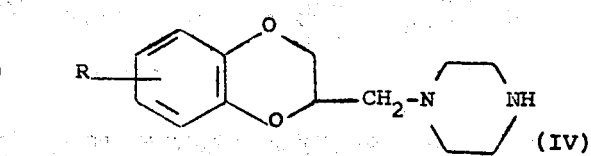

is condensed with a chlorine-containing compound of the formula $$Cl-A_o \qquad (V)$$

wherein $A_o$ is as defined above, in a solvent at the reflux temperature of the said solvent.

One or other of these variants can be chosen depending on the instability of the functional groups present in the radical $A_o$.

Compounds wherein $A_o$ contains an ester group can be formed, for example, from a compound in which $A_o$ contains a hydroxyl group by known methods of esterification, e.g. by reaction with an acid chloride or an acid anhydride.

The solvents used in the reactions indicated above are preferably anhydrous solvents such as, especially, tetrahydrofuran, dimethylformamide, benzene, toluene, xylene, a lower alcohol, or a mixture of such solvents.

The acid addition salts of the compounds of the invention are produced by bringing the bases into contact with an appropriate inorganic or organic acid.

The compounds of formula II can be formed from pyrocatechol or one of its derivatives of formula VI in accordance with the following scheme:

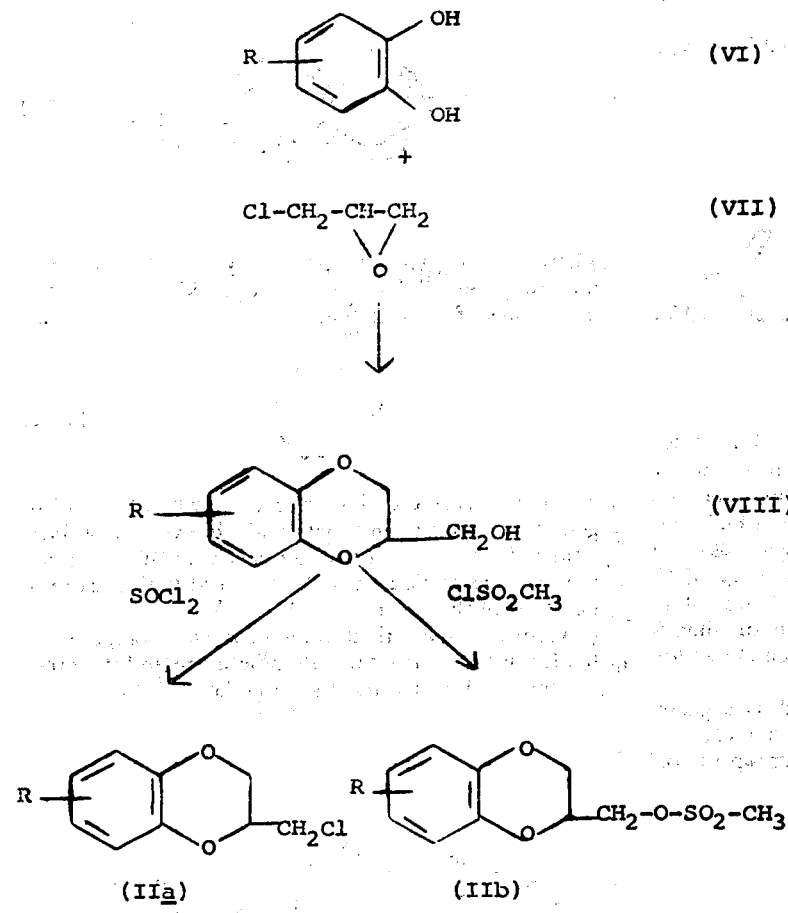

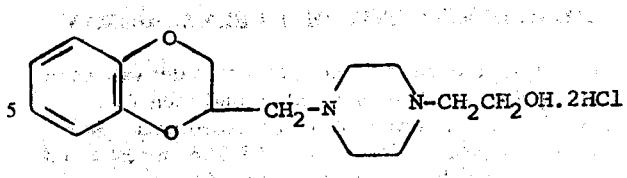

Code number LL 1756.

a. 143 g (1.3 mols) of pyrocatechol, 361 g (3.9 mols) of epichlorohydrin and 500 ml of N sodium hydroxide solution are introduced into a 4 l flask equipped with a stirrer, condenser, thermometer and heating mantle.

The invention includes within its scope pharmaceutical compositions containing, combined with a physiologically tolerated excipient, at least one compound chosen from the group consisting of 1-[2-(1,4-benzodioxanyl)-methyl]-4-(2-hydroxyethyl)-piperazine hemifumarate, the compounds of the formula I and their non-toxic addition salts with acids, as the active ingredient, are proposed.

The following Examples illustrate the invention.

EXAMPLE 1

1-[2-(1,4-Benzodioxanyl)-methyl]-4-(2-hydroxyethyl)-piperazine dihydrochloride (comparison compound).

The mixture is stirred for 1 hour without heating. It is then heated under reflux for 3 hours 30 minutes. The solution is cooled in an ice bath. It is extracted 3 times with 400 ml of diethyl ether. The ether phase is washed twice with 400 ml of N sodium hydroxide solution and then with 200 ml of water. The organic phase is dried overnight over MgSO$_4$. The MgSO$_4$ is filtered off and the ether is evaporated. 202 g (yield: 93.6%) of 2-hydroxymethyl-1,4-benzodioxan are obtained.

b. 202 g (1.21 mols) of 2-hydroxymethyl-1,4-benzodioxan are introduced into a 1 liter flask equipped with a stirrer, condenser and dropping funnel, and 288 g (2.42 mols) of thionyl chloride are run in dropwise. Violent evolution of HCl is observed. The mixture is heated under reflux until HCl ceases to be evolved, that is to say for 1 hour 30 minutes. The mixture is then distilled in vacuo after having driven off the excess thionyl chloride. 175.5 g (yield: 77.2%) of 2-chloromethyl-1,4-benzodioxan are obtained.

c. 245.5 g (1.33 mols) of 2-chloromethyl-1,4-benzodioxan, 156 g (1.2 mols) of 2-ethanol-piperazine, 200 ml of dimethylformamide and 184 g (1.33 mols) of $K_2CO_3$ are introduced into a 2 l Erlenmeyer flask equipped with a stirrer.

The mixture is stirred and heated at 80°C for 6 hours and at 100°C also for 6 hours. The mixture is left to cool and the precipitate is filtered off and washed with 3 times 50 ml of dimethylformamide and then removed. The filtrates are combined and the desired hydrochloride is precipitated by means of 400 ml of an 8.8 N solution of hydrogen chloride in ethanol. The precipitate of hydrochloride is filtered off and washed with ether. The precipitate is dissolved in 300 ml of distilled water, the solution is cooled in an ice bath and 250 ml of sodium hydroxide solution are run in dropwise until the pH is 11 is order to obtain the base. Since the latter is soluble in water, it is extracted with 3 times 300 ml of ether, introducing inorganic salts into the aqueous phase. The ether solution is dried over $MgSO_4$. The ether is evaporated and a clear orange oil is obtained which gradually crystallises.

Since the purity of the product is about 70%, the base is dissolved in a liter of refluxing ethanol. 150 ml of 12 N hydrochloric acid are run in dropwise and this solution is placed in a refrigerator for 1 hour. The solution is filtered, the precipitate is washed with ethanol and the product is dried. 186 g of 1-[2-(1,4-benzodioxanyl)-methyl]-4-(2-hydroxyethyl)-piperazine dihydrochloride are obtained. (Yield 44.1%).

The base is recovered again as indicated above. The base thus purified has a melting point of 62°C.

EXAMPLE 2

1-[2-(1,4-Benzodioxanyl)-methyl]-4-(2-hydroxyethyl)-piperazine hemifumarate

Code number CRL 40040.

10 g of base purified according to Example 1c and 4.06 g of fumaric acid are dissolved in 150 ml of refluxing ethanol. The solution is allowed to cool slowly to ambient temperature and a heavy precipitate appears. It is filtered off and dried and 9 g of hemifumarate are obtained. (Yield 64%).

| Analysis | % N calculated: | 8.32 hemifumarate |
|---|---|---|
|  |  | 7.12 fumarate |
|  | % N found: | 8.05 |

EXAMPLE 3

1-[2-(1,4-Benzodioxanyl)-methyl]-4-(2,3-dihydroxypropyl)-piperazine dihydrochloride.

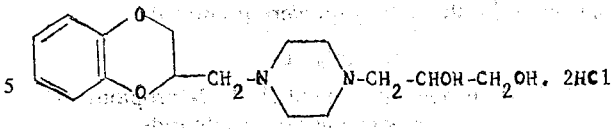

Code number CRL 40034.

18.5 g of 2-chloromethyl-1,4-benzodioxan; 16.9 g of N-(2,3-dihydroxypropyl)-piperazine and 30 ml of dimethylformamide are introduced into a 250 ml Erlenmeyer flask.

The mixture is heated at 80°C for 8 hours. The precipitate is filtered off, washed with DMF and removed. The hydrochloride is precipitated by pouring approximately 30 ml of a 7 N solution of hydrogen chloride in ethanol into the DMF solution. An oil forms. The DMF is decanted and ether is added in order to wash the oil formed. The ether is decanted. The residue is dissolved in the minimum amount of water. The solution is treated with sodium hydroxide solution until the pH is 11. The solution is extracted with ether and the ether phase is dried over $MgSO_4$. The aqueous phase which results from the extraction with ether is separated off and extracted with chloroform, and the chloroform phase collected is then dried over $MgSO_4$. The ether and chloroform phases are evaporated separately. In the ether phase, 5.2 g of oil are obtained [pure in thin layer chromatography, eluant $CHCl_3$ — $CH_3OH$ — $NH_4OH$ (40:40:20)]; in the chloroform phase, 2 g of oil are obtained (impure in thin layer chromatography).

The 5.2 g of oil resulting from the ether phase are dissolved in 100 ml of methanol and the solution is heated under reflux. During the refluxing, 10 ml of a 7 N solution of hydrogen chloride in ethanol are introduced. The mixture is cooled overnight in a refrigerator. On adding acetone, the dihydrochloride precipitates.

5.1 g (yield 13.3%) of product, which is pure in thin layer chromatography [eluant: $CHCl_3$ — $CH_3OH$ — $NH_4OH$ (40:40:20)], are obtained.

EXAMPLES 4 and 5

By following the procedure indicated in Example 1, and replacing pyrocatechol with 4-methyl-pyrocatechol and 4-4-(tertiary butyl)-pyrocatechol, the following products were obtained respectively:

1-[2-(6- or 7-methyl-1,4-benzodioxanyl)-methyl]-4-(2-hydroxyethyl)-piperazine dihydrochloride — code number CRL 4024 — melting at 210°C; and 1-[2-(6- or 7-{tertiary butyl}-1,4-benzodioxanyl)-methyl]-4-(2-hydroxyethyl)-piperazine dihydrochloride — code number CRL 4001 — melting at 180°C.

The uncertainty about the position of the methyl and tertiary butyl substituents of the benzodioxanyl group results from the method of preparation since it is possible for one of the following two cyclisations to take place (with $R_o =$ alkyl)

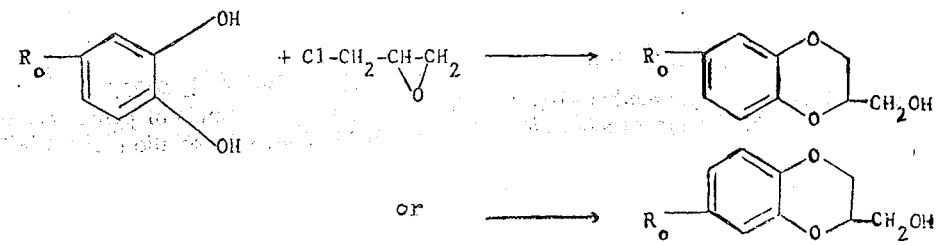

There are strong reasons to believe that derivatives substituted in the 6-position were produced.

EXAMPLE 6

1-[2-(1,4-Benzodioxanyl)-methyl]-4-[2-(propionyloxy)-ethyl]-piperazine dihydrochloride.

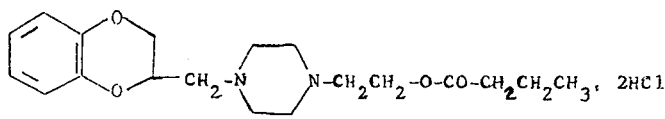

Code number CRL 4011.

A mixture of 5 g (0.192 mol) of propionic anhydride and 13 g (0.037 mol) of LL 1756 (product of example 1c), which is completely soluble in hot acetic acid, is heated to the reflux temperature of acetic acid (75 ml), and refluxing is maintained for 5 hours. After having allowed the reaction mixture to cool, the acetic acid is evaporated and the residual crystalline residue is washed several times with ether and once with ethanol. 11.73 g (yield 77%) of dihydrochloride, which melts at 180°C, are obtained.

This product, analysed by thin layer chromatography, eluant: methanol — acetic acid (80:20), is 98% pure.

EXAMPLE 7

1-[2-(1,4-Benzodioxanyl)-methyl]-4-[2-(acetyloxy)-ethyl]-piperazine dihydrochloride.

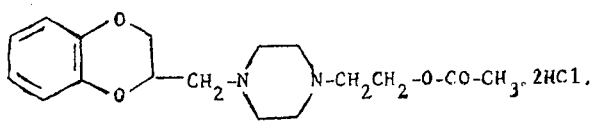

Code number CRL 4010.

5 g of LL 1756 and 3 ml of acetic anhydride in 50 ml of acetic acid are heated at the boiling point for 5 hours. LL 1756 is completely soluble in hot acetic acid.

After cooling, the acetic acid is evaporated and the solid residue is washed several times with ether and then once with ethanol. The product is dried in vacuo at 50°C. 3.47 g (yield 62%) of dihydrochloride, which melts at 180°C (with decomposition), are obtained.

Analysis % of Cl, theory: 18.06%. % of Cl, found: 18.31%.

EXAMPLE 8

1-[2-(1,4-Benzodioxanyl)-methyl]-4-(2-pyrimidinyl)-piperazine dihydrochloride.

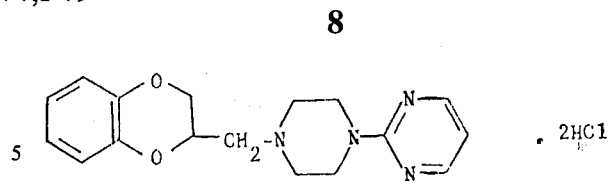

Code number CRL 1767.

A mixture of 34.0 g (0.18 mol) of 2-chloromethyl-1,4-benzodioxan, 19.3 g (0.11 mol) of N-2-pyrimidinyl-piperazine and 25 g (0.18 mol) of $K_2CO_3$ in 30 ml of dimethylformamide is stirred for 48 hours at 100°C. The solution is filtered and the precipitate is washed with DMF. Approximately 55 ml of a 4 N solution of hydrogen chloride in ether are added in order to precipitate the product. 200 ml of ether are added and the mixture is filtered. The precipitate is washed 3 times with 20 ml of ether each time.

The hydrochloride is dissolved in 300 ml of water and this solution is neutralised by means of sodium hydroxide solution until the pH is 11. The base precipitates. The mixture is filtered and the precipitate obtained is washed with distilled water.

25.4 g of base are obtained. It is recrystallised from 300 ml of petroleum ether + 10 ml of acetone. Some insoluble matter in this mixture is again recrystallised from a mixture of 250 ml of petroleum ether and 50 ml of acetone.

The first recrystallisation yields 5.8 g of product and the second yields 10.5 g of product, that is to say 16.3 g in all.

The base obtained is dissolved in 200 ml of methanol and 50 ml of a 5 N solution of hydrogen chloride in ethanol are added. The dihydrochloride precipitates in the refrigerator. It is washed three times with 10 ml of ethanol each time. 17.3 g (yield 40.8%) of white dry 1-[2-(1,4-benzodioxanyl)-methyl]-4-(2-pyrimidinyl)-piperazine dihydrochloride, which melts at 160°C (melting point not instantaneous), are obtained.

EXAMPLE 9

1-[2-(1,4-Benzodioxanyl]-4-(2,6-dimethyl-acetanilido)-piperazine dihydrochloride.

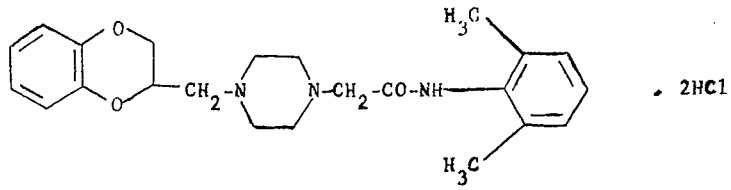

Code number CRL 40035.

a. 66 g (0.6 mol) of pyrocatechol, 600 ml of N sodium hydroxide solution and 166.5 g (1.8 mols) of glycerol epichlorohydrin are mixed. The temperature of the mixture rises to 56°C. From then on, the reaction mixture is heated to the reflux temperature for 5 hours.

The mixture is extracted with 3 × 200 ml of ether. The ether solution is washed with 3 × 200 ml of N sodium hydroxide solution and 2 × 100 ml of water. It is dried over MgSO$_4$. The ether is evaporated. 96.6 g (yield: 96.9%) of 2-hydroxymethyl-1,4-benzodioxan crystals are obtained.

b. 44 g of 2-hydroxymethyl-1,4-benzodioxan and 100 ml of pyridine are introduced into a 250 ml three-necked flask. An orange solution is obtained. Methane sulphonyl chloride is diluted with 50 ml of pyridine (brown solution) and is run dropwise, over the course of 30 minutes, into the reaction mixture described above. At the end of the running-in process, crystals appear. Stirring is then continued for 2 hours. The mixture is filtered and the pyridine is evaporated. The crystals seem to be pyridine hydrochloride. The residual oil, present in the filtrate from which the pyridine has been removed, is taken up again in ethyl acetate and yields a new precipitate which is removed.

Evaporation of the ethyl acetate yields 64.8 g of a yellow oil which is insoluble in water (yield: 86.1%), namely 2-(1,4-benzodioxanyl)-methyl methanesulphonate.

c. 30 ml of xylene and 7 g of anhydrous piperazine are introduced into a 100 ml Erlenmeyer flask with a ground glass neck. Dissolution takes place completely on heating, without stirring. A solution of 2-(1,4-benzodioxanyl)-methyl methanesulphonate is added dropwise to the refluxing xylene; at the end of the running-in process, an oil which is insoluble in xylene is obtained. The mixture is then heated under reflux for 2 hours.

The mixture is then allowed to cool and is extracted with 2 × 20 ml of water and then with 20 ml of 4 N sulphuric acid. The phases resulting from the extraction are placed in an ice bath and are neutralised with sodium hydroxide solution. The mixture is extracted with 3 × 20 ml of ether. The solution is dried over Na$_2$SO$_4$. The solution is filtered and N-[2-(1,4-benzodioxanyl)-methyl]-piperazine dihydrochloride is precipitated by means of a solution of hydrogen chloride in ether. 3.1 g of product (yield: 50.8%) are obtained.

d. 12.83 g of chloro-2,6-dimethyl-acetanilide, 13.48 g of N-[2-(1,4-benzodioxanyl)-methyl]-piperazine dihydrochloride, 8.8 g of K$_2$CO$_3$ and 50 ml of dimethylformamide are introduced into a 250 ml Erlenmeyer flask with a ground glass neck. The mixture is stirred at ambient temperature (20°C) for 24 hours and at 80°C for 1 hour. The precipitate is filtered off, washed with dimethylformamide and removed. The filtrates are combined and 1-[2-(1,4-benzodioxanyl)-methyl]-4-(2,6-dimethylacetanilido)-piperazine dihydrochloride, in DMF, is precipitated by means of 30 ml of a 5.4 N solution of hydrogen chloride in ether. The precipitate is filtered off and drained. It is dissolved in distilled water and treated with sodium hydroxide solution until the pH is 11. The base precipitates. It is filtered off and dissolved in ether. The ether phase is dried over MgSO$_4$ overnight. The desired dihydrochloride is reprecipitated in a mixture of hydrogen chloride and ether. 10 g of product (yield: 28.5%) are obtained.

The results of the pharmacological tests which were undertaken with the products of the formula I have been summarised below. These results demonstrate a vasodilating activity and an α-blocking activity of the adrenergic receptors.

The data relating to toxicity have been summarised in the table below.

TABLE

| Example | LD-50 I.V. in mice (mg/kg) | Maximum non-toxic dose (1) (mg/kg) |
| --- | --- | --- |
| 2 | 97 ± 2 | 90 |
| 3 | 260 ± 11 | >170 |
| 5 | 140 ± 8 | 100 |
| 6 | 109 ± 9 | — |
| 7 | 86 ± 1 | 80 |
| 8 | 145 ± 10 | — |

(1) In mice, by intravenous administration.

Vasodilating properties

During the series of pharmacological tests, the following parameters were used:

Arterial pressure (abbreviated to AP): this parameter, expressed in mm Hg) is evaluated in accordance with the usual conditions.

Arterial resistance: this parameter (expressed in dynes/sec./cm$^{-5}$) is calculated according to the ratio $$\text{Resistance:} \frac{\text{Average AP (mm Hg)} \times 980 \times 1.36 \times 60}{\text{cardiac output (ml/min.)}}$$

Cardiac index: this parameter is expressed in (ml/min.)/kg.

Systolic index: this parameter is equal to the ratio cardiac index/frequency.

Cardiac work: this parameter (expressed in kgm/min.) is calculated according to the relationship: Cardiac work = average AP (mm Hg) × 1.36 = cardiac output (1/min.) × 10$^{-3}$.

Ratio dp/dt: this parameter corresponds to the variation in pressure expressed in mm Hg per second (in English: Rate of rise of left ventricular pressure).

The technique used to measure the ratio dp/dt is as follows:

The cardiac output is determined in Beagle dogs weighing 10 to 15 kg, anesthetised with pentobarbital, by injecting Carbiogreen (1 mg in 0.5 ml) into the right ventricle. A catheter introduced via the carotid artery into the aorta makes it possible to aspirate arterial blood at the rate of 25 ml/min. and to pass it in front of the photoelectric cell of a Beckman cardiodensitometer. The results are interpreted in accordance with the Hamilton method.

In the case of the product of Example 2, the vasodilating properties were investigated in dogs.

On injection into the femoral artery, no effect is observed at doses of less than 100 μg/kg. At a dose of 1 mg/kg, the flow rate of the femoral artery is increased by 34%; it increases by 90% at a dose of 10 mg/kg; it is only increased by 67% at a dose of 20 mg/kg. At these doses, no effect is observed on the arterial pressure AP measured in accordance with the usual conditions.

On injection into the vertebral artery, no effect is observed at doses of less than 1 mg/kg. At a dose of 10 mg/kg, the flow rate increases by 37% and at a dose of 20 mg/kg it only increases by 27%. At these two doses, the arterial pressure decreases respectively by 14 and 28% although no effect had been observed during the injection into the femoral artery.

When administered intravenously, the following results were observed:

In a first test, the product of Example 2, perfused intravenously at a dose of 0.25 mg/kg, increases the vertebral flow rate by 90% at the start of perfusion but only by 14% at the end of perfusion. Additional injections at doses of 0.5 and 5 mg/kg have no effect on the flow rate.

In a second test, a dose of 0.5 mg/kg is injected at the very start and it increases the vertebral flow rate by 135% at the beginning of perfusion and by 58% at the end of perfusion. Subseqent injections at doses of 1 and 2 mg/kg have no effect on the flow rate.

In both these tests, the pulse rate is increased and this effect persists during successive injections.

A third test is carried out by injecting, without stopping, 0.5, 1, 2 and 4 mg/kg, that is to say a total of 7.5 mg/kg. The flow rate of the vertebral artery increases at each of the injections up to the third, whilst the femoral flow rate, which is increased very much by the first injection, decreases during the subsequent injections. The flow rate of the mesenteric artery is uniformly decreased by 25% at each injection.

In another test, the product of Example 2, injected at a dose of 2 mg/kg at the very start, raises the flow rate of the vertebral artery by 87% for more than 1 hour, whilst the flow rate of the femoral artery is only increased greatly during the injection.

The product of Example 2 does not alter the effects of the injection of acetylcholine and isoprenalin nor that of the stimulation of the peripheral vagus, but it reverses the hypertensive effect of adrenalin in a lasting manner.

Furthermore, the coronary flow rate was observed in anaesthetised dogs perfused intravenously at a dose of 5 mg/kg and the following effects were noted: A hypotension of 15 to 38% which can last for more than 2 hours; an increase of 40% in the differential arterial pressure for 1 hour due to lowering of the diastolic arterial pressure; a tachycardia (+ 40%) for a period of more than 2 hours, and an increase in the cardiac work: The maximum intraventricular pressure increases (+ 56%) for 1 hour, the ratio dp/dt increases (+ 180%) for more than 1 hour and the ejection time decreases (25 to 30%); a great increase in the coronary flow rate with the maximum effect (+ 200%) being shown after 1 hour, whilst 2 hours after the injection the flow rate is still increased by 75%.

To summarise, the product of Example 2 acts as an α-lytic product, which can dilate either the vertebral artery or the femoral artery or both. Moreover, it possesses tachycardiac properties at low doses; at a higher dose, it is hypotensive. It increases the cardiac work and, in parallel fashion, it increases the coronary irrigation.

In animal pharmacology, the active doses are approximately 1/100th and even 1/200th of the LD 50 I.V. in mice.

In clinical studies, good results were obtained in man by administering tablets such as:

1-[2-(1,4-Benzodioxanyl)-methyl]-4-
(2-hydroxyethyl)-piperazine hemifumarate    50 mg
Excipient, q.s.p.                           500 mg to 1,000 mg
or injectable ampoules such as:
1-[2-(1,4-Benzodioxanyl)-methyl]-4-
(2-hydroxyethyl)-piperazine hemifumarate    10 mg
NaCl solution, of concentration 9 g/l, q.s.p. 3 ml ampoule.

The product of Example 8 was investigated in dogs anaesthetised by means of Nembutal. The product of Example 8 was perfused intravenously over the course of 5 minutes at doses of 2.5 and 5 mg/kg. At a dose of 2.5 mg/kg, an increase in the differential arterial pressure (+ 50%), a tachycardia (+ 19%), a slight femoral vasodilating effect (+ 19%) and a decrease in the vertebral flow rate (19%), and practically no effect on the mesenteric flow rate, are observed.

With the product of Example 8, the hypertensive effect of adrenalin is reversed, and this manifests itself in an α-blocking action.

When administered orally, the product of Example 8 does not alter the flow rate of the femoral artery; nor that of the vertebral artery, at doses of less than 100 μg/kg. At higher doses, that is to say of 1 to 10 mg/kg (at a dose of 10 mg/kg the product passes into the general circulation), a rise in the flow rates is noted: + 200% in the case of the femoral flow rate and + 60% in the case of the vertebral flow rate for 30 minutes.

Cardiovascular properties of the product of Example 3

When administered intravenously to dogs at doses ranging from 1 mg to 13 mg/kg, the following results are observed:

An increase in the differential AP,
little effect on the AP or a slight hypotension,
a rise in the pulse rate which does not exceed 25%,
an increase in dp/dt with a shortening of the ejection time,
the cardiac output is scarcely changed, and
no effect on the vertebral flow rate;
when administered intraduodenally, the product passes easily through the intestinal barrier; at doses of 10 and 50 mg/kg administered intraduodenally, the variations described after intravenous injection are found again. A dose of 10 mg/kg administered intraduodenally leads to a reversal of the hypertensive effect of adrenalin.

In conclusion, the product of Example 3 is an α-blocking agent which passes through the intestinal barrier.

When administered to man in the form of tablets containing 20 mg, (at the rate of) 2 to 3 per day, it gave good results in vascular complaints.

Vasodilating properties of the product of Example 5.

Local administration: When injected locally into the femoral artery or into the vertebral artery of dogs, the product increases both these flow rates in proportion to the doses, but with a preference for the femoral flow rate.

General administration:
Intravenus administration.
2 dogs received the product of Example 5 successively at doses of 3.75 and 15 mm/kg, by intravenous administration. The following results are observed:

A femoral vasodilating action for 10 to 15 minutes, not proportional to the dose, maximum (+ 60%) from 3.5 mg/kg;
no vertebral dilating action;
no effect on the AP up to 15 mg/kg; and
a bradycardia at this last dose.

When administered intraduodeanlly, no vasodilating effect is observed in dogs receiving successively 3.5, 7, 15 and 35 mg/kg whilst the pulse rate decreases from 7 mg/kg.

To summarise, the product of Example 5 exerts an exclusively peripheral and very moderate vasodilating effect. It also possesses an analgesic activity of the morphine type when it is injected subcutaneously.

Vasodilating properties of the product of Example 6

In the case of intravenous administration, the tests were carried out on 4 anaesthetised dogs. The product is perfused intravenously over the course of 5 minutes at doses of 2.5, 5 and 10 mg/kg and, in one test, is administered intraduodenally at a dose of 10 mg/kg. A hypotensive effect proportional to the dose is observes. The pulse rate either is not altered (2 tests) or is increased. The intraventricular pressure is decreased as is the ratio dp/dt. The femoral flow rate is increased in the tests wherein an increase in the pulse rate is observed and this effect disappears in 15 minutes.

The vertebral flow rate only increases in one of the two tests wherein the pulse rate was increased.

The product is α-blocking from a dose of 5 mg/kg administered intravenously.

When administered intra-arterially, the product of Example 6 is injected directly into the femoral artery. The flow rate is increased by 200% from a dose of 10 μg. Higher doses up to and including 10 mg do not produce a greater vasodilation.

In conclusion, the product of Example 6 is an α-blocking product from a dose of 5 mg/kg administered intravenously. When it increases the femoral flow rate, this effect is of short duration and is not reproducible. The product passes through the intestinal barrier and the activity is found again at 10 mg/kg administered intraduodenally. The vasodilating effect produced by a femoral intra-arterial injection is maximal from the very start and cannot be increased by higher doses. The mechanism of the vasodilating effect thus seems to be exclusively an alphalytic mechanism.

Cardiovascular action of the product of Example 7 in anaesthetised dogs

The adrenolytic action was investigated and demonstrated in dogs from a dose of 2.5 mg/kg administered intravenously (reversal of the hypertension due to adrenalin). From this dose, a hypotension and a decrease in the left ventricular pressure, in the ratio dp/dt and in the systolic ejection time are noted, and this applied in the case of both dogs. The pulse rate does not vary markedly.

In conclusion, it is apparent from these tests that the product of Example 7 is α-lytic.

Furthermore, the dihydrochloride of Example 1 (LL 1756) and the corresponding free base described by TOLDY and colleaques were compared with the products of the invention.

On a pharmacodynamic plane, when the said free base is administered orally to dogs it does not show any α-blocking activity since it does not make it possible to counteract the hypertensive effects of adrenalin, as is the case of the products of the invention and particularly of the product of Example 2, the hemifumarate, which decreases the said effects at a dose of 5 mg/kg, inhibits them strongly at a dose of 7 mg/kg and overcomes the α+ effect of adrenalin at a dose of 10 mg/kg.

LL 1756 is also α-blocking when administered parenterally, but in clinical tests, LL 1756 and the corresponding free base, both of which are soluble in water, caused vertigo in the majority of cases, whilst the products of the invention did not give rise to any vertigo.

I claim:

1. The compound 1-[2-(1,4-benzodioxanyl)-methyl]-4-(2-hydroxyethyl)-piperazin hemifumarate.

2. The compound 1-[2-(1,4-benzodioxanyl)-methyl]-4-(2,3-dihydroxypropyl)-piperazine dihydrochloride.

3. The compound 1-[2-(6- or 7-methyl-1,4-benzodioxanyl)-methyl]-4-(2-hydroxyethyl)-piperazine dihydrochloride.

4. The compound 1-[2-(6- or 7-{tertiary butyl}-1,4-benzodioxanyl)-methyl]-4-(2-hydroxyethyl)-piperazine dihydrochloride.

5. The compound 1-[2-(1,4-benzodioxanyl)-methyl]-4-[2-(propionyloxy)-ethyl]-piperazine dihydrochloride.

6. The compound 1-[2-(1,4-benzodioxanyl)-methyl]-4-[2-(acetyloxy)-ethyl]-piperazine dihydrochloride.

7. The compound 1-[2-(1,4-benzodioxanyl)-methyl]-4-(2-pyrimidinyl)-piperazine dihydrochloride.

8. The compound 1-[2-(1,4-benzodioxanyl)-methyl]-4-(2,6-dimethylacetanilido)-piperazine dihydrochloride.

* * * * *